United States Patent
McCarthy (10) Patent No.: US 7,294,148 B2
(45) Date of Patent: Nov. 13, 2007

(54) ANNULOPLASTY RING FOR MITRAL VALVE PROLAPSE

(75) Inventor: Patrick M. McCarthy, Chicago, IL (US)

(73) Assignee: Edwards Lifesciences Corporation, Irvine, CA (US)

( * ) Notice: Subject to any disclaimer, the term of this patent is extended or adjusted under 35 U.S.C. 154(b) by 611 days.

(21) Appl. No.: 10/834,556

(22) Filed: Apr. 29, 2004

(65) Prior Publication Data

US 2005/0246014 A1    Nov. 3, 2005

(51) Int. Cl.
*A61F 2/24* (2006.01)
(52) U.S. Cl. ............... 623/2.36; 623/2.41; 623/2.38
(58) Field of Classification Search ............... None
See application file for complete search history.

(56) References Cited

U.S. PATENT DOCUMENTS

| | | | |
|---|---|---|---|
| 3,656,185 A | 4/1972 | Carpentier | |
| 4,164,046 A | 8/1979 | Cooley | |
| 4,217,665 A | 8/1980 | Bex et al. | |
| 5,061,277 A | 10/1991 | Carpentier et al. | |
| 5,104,407 A | 4/1992 | Lam et al. | |
| 5,496,336 A | 3/1996 | Cosgrove et al. | |
| 5,607,471 A * | 3/1997 | Seguin et al. ............. | 623/2.36 |
| 5,776,189 A | 7/1998 | Khalid | |
| 6,102,945 A | 8/2000 | Campbell | |
| 6,159,240 A | 12/2000 | Sparer et al. | |
| 6,183,512 B1 | 2/2001 | Howanec, Jr. et al. | |
| 6,250,308 B1 | 6/2001 | Cox | |
| 6,258,122 B1 | 7/2001 | Tweden et al. | |
| 6,419,696 B1 | 7/2002 | Ortiz et al. | |
| 2002/0129820 A1 | 9/2002 | Ryan et al. | |
| 2002/0169504 A1 | 11/2002 | Alferness et al. | |
| 2003/0033009 A1 | 2/2003 | Gabbay | |
| 2003/0083742 A1 | 5/2003 | Spence et al. | |
| 2003/0093148 A1 * | 5/2003 | Bolling et al. ............. | 623/2.36 |
| 2004/0006384 A1 | 1/2004 | McCarthy | |

FOREIGN PATENT DOCUMENTS

| | | |
|---|---|---|
| EP | 0338 994 | 10/1989 |
| EP | 1 034 753 | 9/2000 |

(Continued)

OTHER PUBLICATIONS

PCT International Search Report (PCT/US2005/0014585) mailed Sep. 29, 2005.

(Continued)

*Primary Examiner*—Corrine McDermott
*Assistant Examiner*—Christopher Daniel Prone
(74) *Attorney, Agent, or Firm*—Rajiv Yadav; Guy L. Cumberbatch (57) ABSTRACT

A mitral annuloplasty ring that has an outward and an upward posterior bow. The ring defines a closed, modified oval shape with a minor-major axis dimension ratio of between about 3.3:4 to 4:4. The ring is made of a material that will substantially resist distortion when subjected to the stress imparted thereon when the ring is implanted in the mitral valve annulus of an operating human heart. As a result, the annuloplasty ring corrects for pathologies associated with mitral valve prolapse, or Barlow's syndrome, in which the leaflets tend to be elongated or floppy.

40 Claims, 5 Drawing Sheets

FOREIGN PATENT DOCUMENTS

WO    WO 01/26586    4/2001

OTHER PUBLICATIONS

Melo et al., "Atrioventricular Valve Repair Using Externally Adjustable Flexible Rings," The Journal of Thoracic Cardiovascular Surgery, vol. 110, No. 5, 1995.

Alonso-Lei, M. D., et al., "Adjustable Annuloplasty For Tricuspid Insufficiency," The Annals of Thoracic Surgery, vol. 46, No. 3, pp. 368-369, Sep. 1988.

Carpentier-Edwards Classic Annuloplasty Ring with Duraflo Treatment Models 4425 and 4525 for Mitral and Tricuspid Valvuloplasty, Baxter Health care Corporation, 1998.

* cited by examiner

ANNULOPLASTY RING FOR MITRAL VALVE PROLAPSE

FIELD OF THE INVENTION

The present invention refers to a prosthetic annuloplasty ring for a mitral valve, in particular for correcting pathologies associated with Barlow's syndrome or myxomatous disease.

BACKGROUND OF THE INVENTION

In the operation of the heart, returning blood enters the right atrium and passes through the tricuspid valve into the right ventricle. From there, blood is pumped through the pulmonary valve and the pulmonary artery to the lungs. Oxygenated blood enters the left atrium and passes into the left ventricle through the mitral valve. Healthy mitral valve leaflets "coapt" or meet near the middle of the blood flow path and are attached to the interior of the left ventricle by a number of stringy chordae tendinae CT. During systole, the mitral valve closes and the aortic valve opens, thus preventing blood from regurgitating into the left atrium and forcing blood into the aorta, and from there throughout the body. Because of the high pressures associated with the left ventricle during systole, proper mitral valve function to prevent back flow through the system is extremely important.

Mitral regurgitation is one of the most common valvular malfunctions in the adult population. Mitral valve prolapse is the most common cause of mitral regurgitation in North America and is believed to affect at least 5 to 10 percent of the population in the U.S. Women are affected about twice as often as men. Mitral valve prolapse has been diagnosed as Barlow's disease, billowing or balloon mitral valve, floppy mitral valve, floppy-valve syndrome, myxomatous mitral valve, prolapsing mitral leaflet syndrome, or systolic click-murmur syndrome. Some forms of mitral valve prolapse seem to be hereditary, though the condition has been associated with Marfan's syndrome, Grave's disease, and other disorders.

Barlow's disease is characterized by myxoid degeneration and appears early in life, often before the age of fifty. Patients typically present with a long history of systolic murmur and may experience valve infection, arrhythmias and atypical chest pain. Some cases are asymptomatic, but a pronounced midsystolic click with or without late systolic murmur, usually indicates the presence of this disorder. South African cardiologist John B. Barlow was the first to interpret this auscultation syndrome, known for decades as an expression of a mitral valve prolapse. In Barlow's disease, one or both leaflets of the mitral valve protrude into the left atrium during the systolic phase of ventricular contraction. The valve leaflets are thick with considerable excess tissue, producing an undulating pattern at the free edges of the leaflets. The chordae are thickened, elongated and may be ruptured. Papillary muscles are also occasionally elongated. The annulus is dilated and sometimes calcified.

Figure 1:
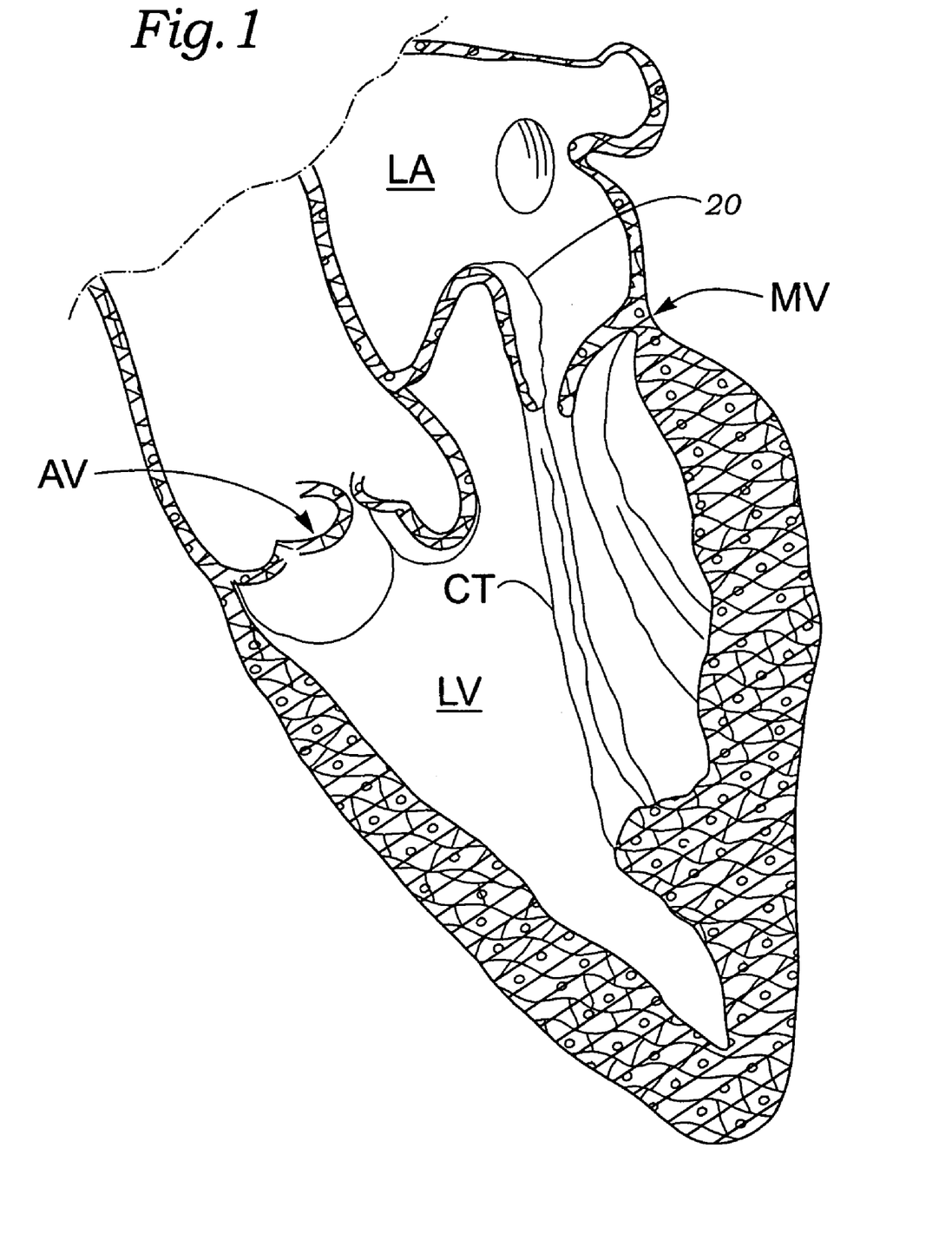
FIG. 1 is an enlarged sectional view of the left ventricle of a human heart illustrating one configuration of distended mitral valve leaflets seen with mitral valve prolapse.

FIG. 1 is an enlarged view of the left ventricle LV illustrating mitral valve prolapse, such as with Barlow's syndrome. One of the leaflets 20 of the mitral valve Mv is shown thickened and lengthened from its normal configuration. As a result, the leaflet 20 is shown flopping upward into the left atrium LA. This excess tissue, or redundancy, often prevents the anterior and posterior leaflets from properly coapting, resulting in mitral regurgitation.

In patients with degenerative mitral valve disease, valve repairs using mitral valvuloplasty valve reconstruction, or annuloplasty have been the standards for surgical correction of mitral regurgitation and have provided excellent long-term results. A rigid support ring (e.g., Carpentier-Edwards Classic™), a semi-flexible ring (e.g., Carpentier-Edwards Physio™), or a flexible ring (e.g., Cosgrove-Edwards™) may be used. Other repair techniques include: quadrangular resection of the prolapsing portion of the posterior leaflet; transposition of the posterior leaflet to the anterior leaflet to correct anterior-leaflet prolapse; commissurotomy combined with ring annuloplasty; replacement of a chordae tendinae with sutures; and plication (or resection) of the anterior leaflet. A commonly used repair is the so-called "sliding technique" introduced by Dr. Alain Carpentier, which involves quadrangular resection followed by cutting the posterior leaflet and reconstruction to shorten this leaflet. The advantages of repair over replacement have been widely demonstrated; however, studies have shown that mitral valve repair is performed in less than half of surgical procedures involving the mitral valve, and even fewer repairs are performed in patients with complex mitral regurgitation (e.g., Barlow's disease, bileaflet prolapse and annular calcification). Despite adequate tissue resection and placement of an annuloplasty ring or band, patients may have residual mitral regurgitation associated with systolic anterior motion (SAM) of the anterior leaflet. SAM occurs when the elongated leaflet is pulled into the left ventricular outflow tract (LVOT). This leads to partial LVOT obstruction and hemodynamic instability. This scenario is not an uncommon incident following an otherwise successful mitral valve repair and can be very difficult to treat with existing repair techniques and devices, and may require mitral valve replacement rather than the preferred of valve repair.

Figure 2A:
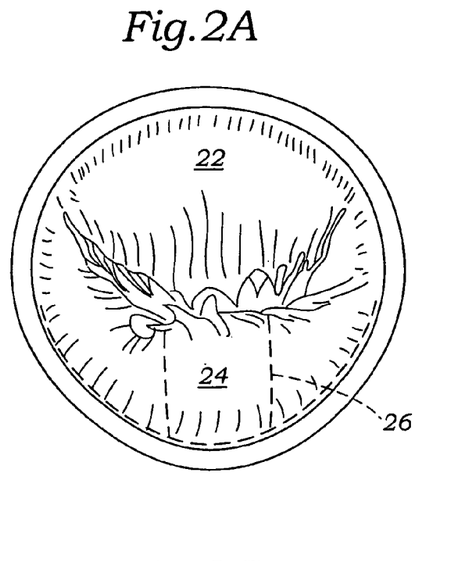
FIGS. 2A-2F are a series of plan views of a prior art surgical procedure for correcting a mitral valve that exhibits symptoms of mitral valve prolapse.
Figure 2B:
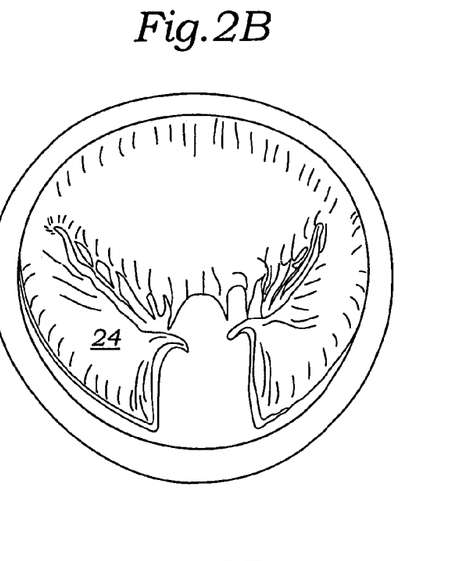
Figure 2C:
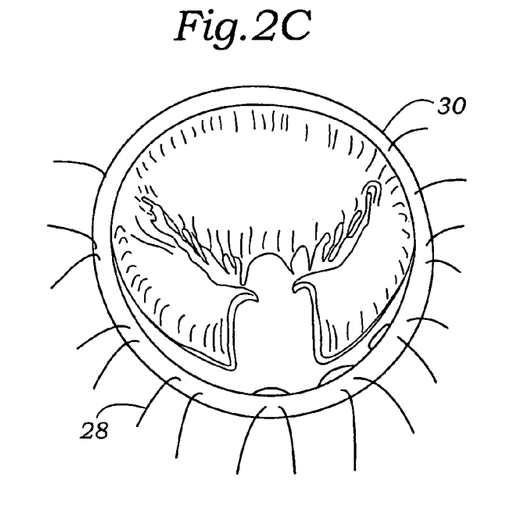
Figure 2D:
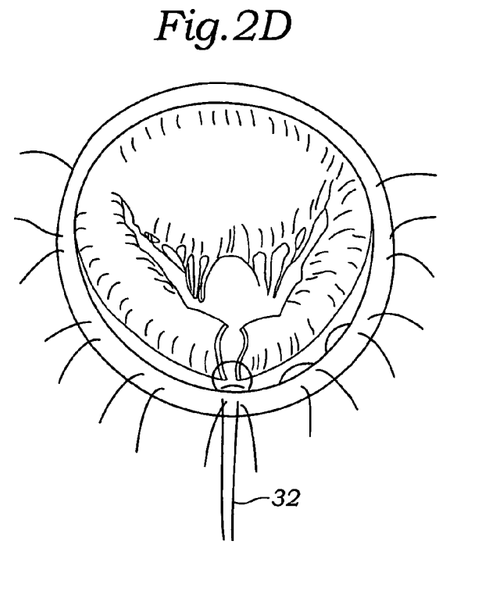
Figure 2E:
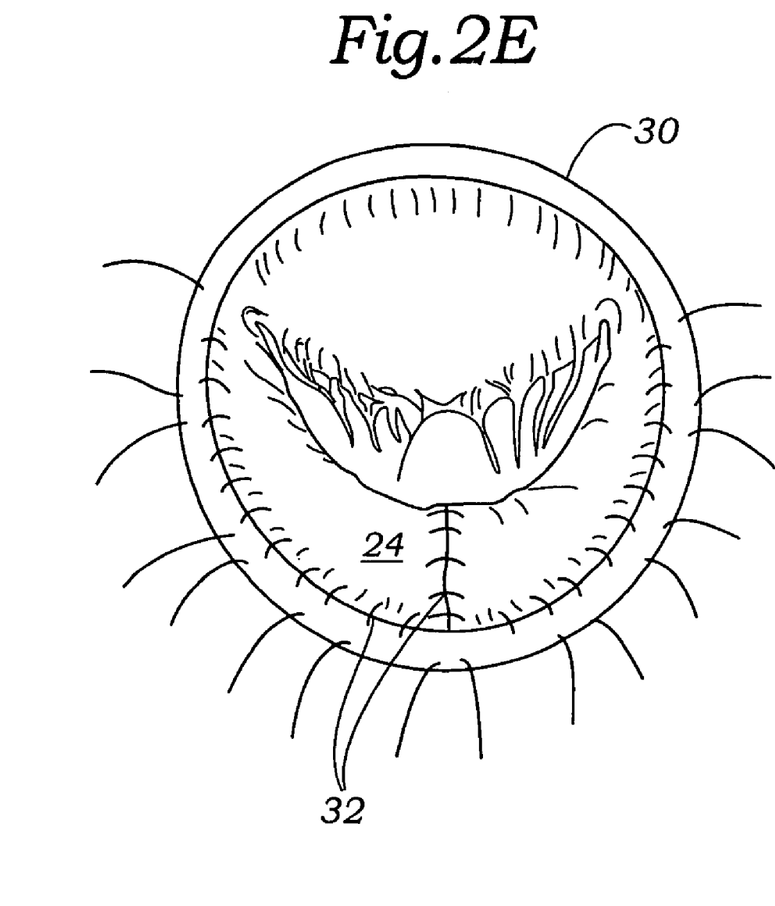
Figure 2F:
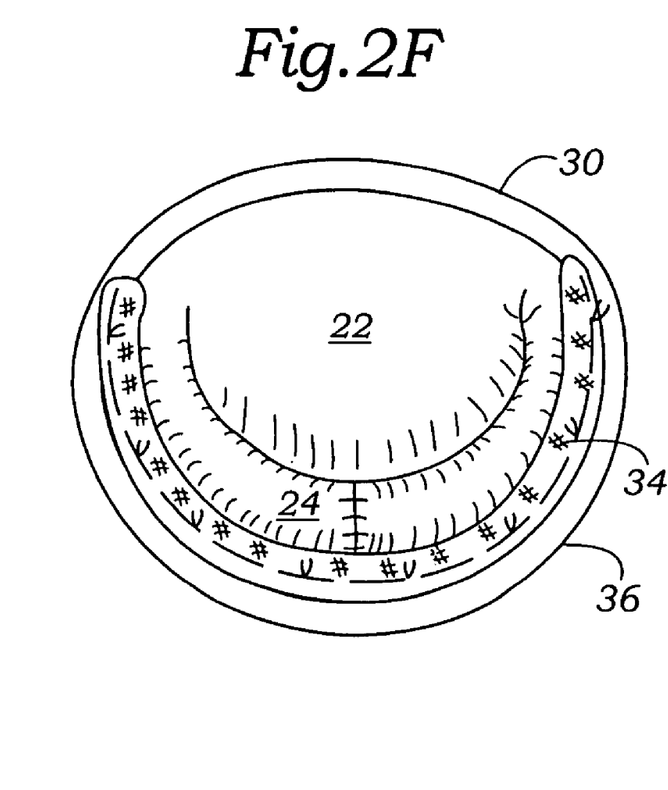

One example of a prior art surgical resection technique for correcting mitral valve prolapse, or Barlow's syndrome, is seen in the sequence of FIGS. 2A-2F. FIG. 2A is a plan view of the mitral valve annulus in which the anterior leaflet 22 and posterior leaflet 24 do not properly coapt in the middle of the annulus. A somewhat smile-shaped gap is seen between the two leaflets. As mentioned above, this condition can result from a number of pathologies, though the particular pathology corrected by the present invention is that which typically results from Barlow's syndrome. The surgical technique involves resecting a portion of the posterior leaflet 24 by first cutting along the dashed lines 26. FIG. 2B shows the posterior leaflet 24 after the portion indicated in FIG. 2A has been resected and an incision for sliding annuloplasty has been performed FIGS. 2C-2E illustrate a progression of suturing operations in which first stabilizing sutures 28 are passed through the annulus 30 and then a plurality of fixation sutures 32 are used to reapproximate the posterior leaflet 24, thus shortening the posterior leaflet relative to the annulus 30. Finally, in FIG. 2F, an annuloplasty ring 34 has been implanted around the posterior aspect 36 of the annulus 30, generally corresponding to the perimeter of the posterior leaflet 24. A comparison of the size of the annulus 30 in FIGS. 2E and 2F illustrates the effect of the addition of the ring 34. That is, the annulus circumference has been reduced. More importantly though, the leaflets 22, 24 are shown properly coapting without the aforementioned gap.

In early 90's, Dr. Ottavio Alfieri introduced the concept of edge-to-edge heart valve repair. This repair technique consists of suturing the edges of the leaflets at the site of regurgitation, either at the paracommissural area (eg: A1-P1 segments: para commissural repair) or at the middle of the valve (e.g.: A2-P2 segments: double orifice repair). Three patents disclosing various devices for performing such edge-to-edge procedures are U.S. Pat. No. 6,165,183 to Kuehn, et al., U.S. Pat. No. 6,269,819 to Oz, et al., and U.S. Pat. No. 6,626,930 to Allen, et al. Recently, the edge-to-edge technique has been used in conjunction with annuloplasty procedures for treating the pathology seen with Barlow's disease. The underlying bases for these techniques are to eliminate the primary regurgitant area by suturing the leaflet edge and decreaseing leaflet mobility, and to correct leaflet redundancy, force coaptation, and restrict leaflet motion.

Despite accepted treatments for correcting mitral valve prolapse, in particular Barlow's syndrome, there is a need for a simpler and more effective approach, preferably one which avoids the need for sliding annuloplasty. Sliding annuloplasty adds technical and skill intensive barriers that limit widespread adoption of mitral valve repair.

SUMMARY OF THE INVENTION

The present invention provides a mitral annuloplasty ring comprising a ring body made of a material that will substantially resist distortion when subjected to the stress imparted thereon by an operating human heart. The ring body defines an anterior segment and a posterior portion opposite the anterior segment. Right and left sides are located between the anterior segment and posterior portion. A central flow axis has an upward direction and a downward direction, the downward direction corresponding to the direction of blood flow through the mitral valve annulus when the annuloplasty ring is implanted. The ring body has a modified oval shape with a minor axis extending between the anterior segment and posterior portion, and a major axis extending between the sides. A bow in the posterior portion of the ring body extends both radially outward and axially upward.

In accordance with another aspect, a mitral annuloplasty ring of the present invention comprises a ring body made of a material that will substantially resist distortion when subjected to the stress imparted thereon after implantation in the mitral valve annulus of an operating human heart. The ring body defines a rounded ring body having an anterior segment and a posterior portion. The ring body is oriented about a central flow axis, the flow axis defining an upward direction and a downward direction, the downward direction corresponding to the direction of blood flow through the mitral valve annulus. The posterior portion the ring body bows upward out of a plane perpendicular to the central flow axis and also has a radially outward curve more pronounced than adjacent sections.

In accordance with a still further aspect of the invention, a mitral annuloplasty ring comprises a ring body made of a material that will substantially resist distortion when subjected to the stress imparted thereon after implantation in the mitral valve annulus of an operating human heart, the ring body defines a modified oval-shaped ring body oriented about a central flow axis, the flow axis defining an upward direction and a downward direction, the downward direction corresponding to the direction of blood flow through the mitral valve annulus from the left atrium to the left ventricle, and wherein in plan view as seen along the flow axis the ring body has a major axis perpendicular to a minor axis, the major and minor axes being perpendicular to the flow axis. The ring body having in atrial plan view an anterior segment generally defined between an anterolateral trigone and a posteromedial trigone, and a posterior portion around the remaining periphery of the ring body and between the trigones, the posterior portion being divided into three sequential segments, $P_1$, $P_2$, and $P_3$ starting from the anterolateral trigone and continuing in a counterclockwise direction, the segments generally corresponding to the size of the native posterior leaflet cusps, wherein the minor axis intersects both the anterior segment and the $P_2$ segment of the posterior portion. The ring body lies substantially in a plane defined by the major and minor axes or in a saddle-shaped three-dimensional surface except for the $P_2$ segment of the posterior portion located which is deflected upward and outward with respect to the adjacent sections of the ring body.

In a ring of the present invention, an axial height h of the upward bow or deflection exceeds about 3 mm, more preferably between about 3-10 mm. In atrial plan view as seen along the flow axis, the ring body has a major axis perpendicular to a minor axis, the major and minor axes being perpendicular to the flow axis, and the minor-major dimension ratio is preferably between about 3.3:4 (82.5%) and 4:4 (100%), more preferably about 3.5:4 (87.5%). The bow may be centered about the minor axis and have an angular extent of between about 90-110°, for example about 100°.

The ring body has an anterior segment generally defined between an anterolateral trigone and a posteromedial trigone, and a posterior portion around the remaining periphery of the ring body and between the trigones. The posterior portion is divided into three sequential segments, $P_1$, $P_2$, and $P_3$, starting from the anterolateral trigone and continuing in a counterclockwise direction. Desirably, the bow in the posterior portion is wholly within the middle segment $P_2$ of the posterior portion of the ring. Alternatively, the bow in the posterior portion may be within the middle segment $P_2$ and extend into at least one other segment $P_1$ or $P_3$ of the posterior portion of the ring.

DESCRIPTION OF THE PREFERRED EMBODIMENTS

The present invention provides a novel annuloplasty ring for correcting pathologies associated with mitral valve prolapse, also known by a number of other names given above, including Barlow's syndrome. With this pathology, the mitral valve leaflets are distended, lengthened, thickened, or in general have become loose and floppy such that they do not properly coapt. In contrast to prior repair techniques, the annuloplasty ring of the present invention reduces or eliminates the need for a sliding annuloplasty. Furthermore, instead of attempting to constrict the mitral annulus by the addition of an annuloplasty ring that is under-sized with respect to the existing annulus, the present invention accommodates the excess material of the leaflets by providing a larger support ring than has previously been utilized. Typical annuloplasty support rings have a long or major dimension and a short or minor dimension, with the conventional ratio of the minor to major dimension being approximately 3:4 (75%). The present invention provides an annuloplasty ring that has a significantly increased minor to major dimension ratio of approximately 3.5:4 (87.5%).

Annuloplasty rings of the present invention are desirably made of material(s) that will substantially resist distortion when subjected to the stress imparted thereon by the mitral valve annulus of an operating human heart. In this sense, "distortion" means substantial deformation from a predetermined shape. Thus, at least the posterior aspect of the annuloplasty rings is relatively rigid, as opposed to flexible as those made substantially of silicone. A number of materials can be utilized that will perform this function, including various bio-compatible polymers and metals and/or alloys. Certain polyesters that resist distortion and also rapid degradation within the body may be used (a material that degrades more slowly, however, may provide the required initial support). In a preferred embodiment, at least an inner core of the annuloplasty rings of the present invention is made of a suitable metal, such as titanium or its alloys, or ELGILOY made by Elgiloy, L.P. of Elgin, Ill., U.S.A. The core may be one piece, or may include a plurality of concentric or otherwise cooperating elements. The addition of a silicone tube around the core and a suture-permeable fabric on the exterior of the ring are also contemplated.

Figures 3A, 3B:
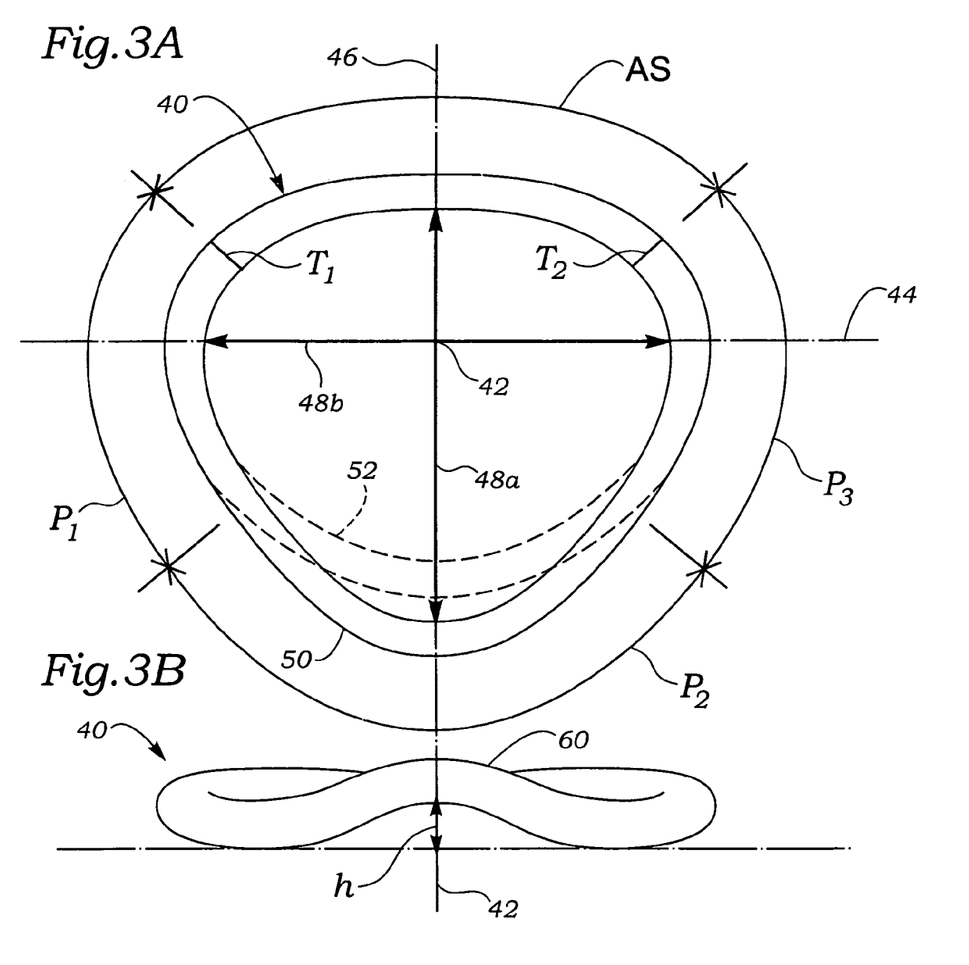
FIGS. 3A-3B are top plan and posterior elevational views, respectively, of a mitral annuloplasty ring of the present invention having an outward and upward posterior bow.

With reference now to FIGS. 3A and 3B, an exemplary mitral annuloplasty ring 40 is shown in plan and posterior elevational views, respectively. The annuloplasty ring 40 has a modified oval shape (closed) in plan view and is oriented about a central flow axis 42. The flow axis 42 defines an upward direction and a downward direction, the downward direction corresponding to the direction of blood flow through the mitral valve annulus from the left atrium to the left ventricle. In this context, upward and downward corresponds to the top and bottom of the page relative the rings as seen in FIG. 3B. Looking along the flow axis 42 in FIG. 3A, the ring 40 has a major axis 44 perpendicular to a minor 46 axis, the major and minor axes being perpendicular to the flow axis.

A minor axis dimension 48a is shown extending across the interior of the ring 40 in plan view. Likewise, the major axis dimension 48b is shown extending horizontally across the interior of the ring. Desirably, the ratio of the minor axis dimension 48a to the major axis dimension 48b is about 3.5:4 (87.5%).

For purpose of further definition, a pair of trigone markers $T_1$ and $T_2$ are shown on the ring 40 corresponding to the approximate location of the fibrous trigones of the mitral annulus when the ring is implanted. An anterior segment extends around the upper portion of the ring 40 in FIG. 3A between the trigone markers $T_1$, $T_2$. When the ring 40 is implanted, the anterior segment will coincide with the anterior aspect of the mitral annulus. The anterior segment is shown planar, though it may be upwardly curved or bowed to better conform to the anterior aspect of the native annulus.

The remainder of the ring 40 aside from the anterior segment will be termed the posterior portion, and is shown broken up into three sequential segments denoted $P_1$, $P_2$, and $P_3$ (moving counter-clockwise from the first trigone marker $T_1$). The precise angular dividing line between these three segments is not standardized, though they are intended to generally correspond to the three visible cusps of the posterior leaflet of the mitral valve. In an exemplary embodiment, the three segments are approximately equal in angular dimension, and the middle segment $P_2$ is symmetric about the minor axis 46.

The annuloplasty ring 40 has a modified oval shape in plan view because of an outward bow 50 within the middle segment $P_2$ of the posterior portion of the ring. Stated another way, the middle segment $P_2$ of the posterior portion of the ring has an outward curve (convexity) more pronounced than adjacent sections (which are also convex) (in this sense, "more pronounced" means an outward bow with a smaller radius than adjacent convex sections). A dashed outline 52 of a conventional 3:4 ratio annuloplasty ring is shown to illustrate the outward bow 50 of the present ring 40. As mentioned above, the outward bow 50 preferably results in a minor-major dimension ratio of 3.5:4 (87.5%), although the present invention encompasses rings having an outward bow 50 that produces ratios of between 3.3:4 (82.5%) and 4:4 (100%).

It is important to note that although the minor axis dimension 48a increases relative to conventional rings (i.e., dashed outline 52), the major axis dimension 48b will remain substantially the same. Furthermore, although the outward bow 50 is shown within the middle segment $P_2$ of the posterior portion of the ring, the posterior portion below the major axis 44 may be affected. That is, the outward bow 50 may extend into one or both of the first and third segments $P_1$ and $P_3$ of the posterior portion. In a preferred embodiment, however, the annuloplasty ring 40 only diverges from a conventional oval- or D-shaped ring (such as the Carpentier-Edwards classic ring™) within the middle segment $P_2$. In an exemplary embodiment, the angular extent of the outward bow 50 centered about the central axis 42 is between 90-110°, and more preferably about 100°.

In conjunction with the outward bow 50, the annuloplasty ring 40 also includes an upward bow 60 seen in FIG. 3B. The term "upward bow" refers to either an upward divergence from a planar ring, or an upward divergence from a so-called "saddle-shaped" ring. Therefore, the present invention encompasses both planar and saddle-shaped rings having an outward and upward posterior bow.

A height h of the upward bow 60 is indicated in FIG. 3B and desirably exceeds about 3 mm, preferably more than about 5 mm, and most preferably between about 3-10 mm. The upward bow 60 may or may not be formed in the ring 40 around the same angular extent as the outward bow 50. In a preferred embodiment, both the outward bow 50 and upward bow 60 start and end at the same location around the ring 40, which is preferably within an included angle of about 90-110° centered along the minor axis 46. Alternatively, the upward bow 60 may extend farther around the ring into the first and third segments $P_1$ and $P_3$ of the posterior portion.

Figure 4:
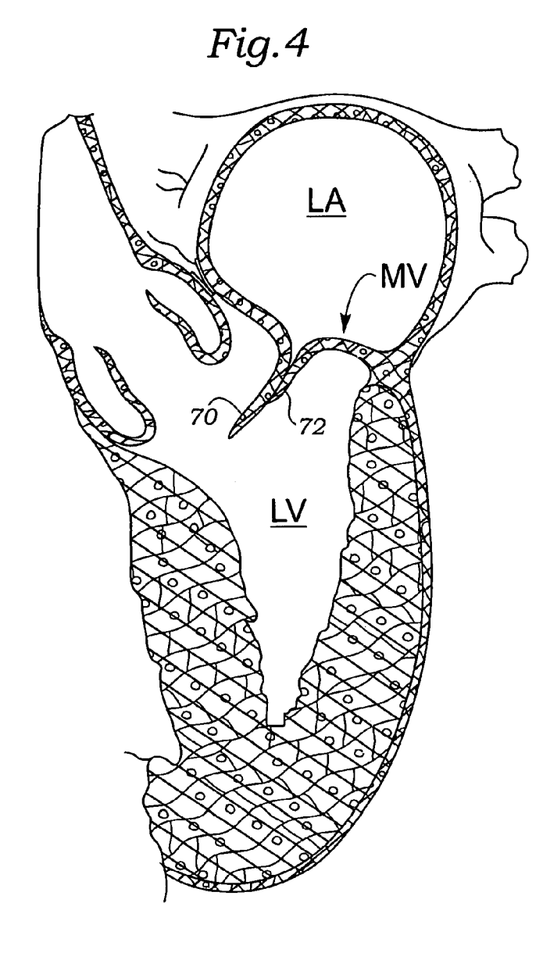
FIG. 4 is an enlarged sectional view of the left ventricle of a human heart illustrating another possible configuration of distended mitral valve leaflets seen with mitral valve prolapse.

FIG. 4 is a further sectional illustration of the left ventricle LV showing a different configuration of the leaflets of the mitral valve in the presence of Barlow's syndrome than that shown in FIG. 1. In this figure, the chordae tendinae are not shown for clarity. One of the leaflets 70 is shown extending much farther into the left ventricle LV than the other leaflet 72. In this condition, the leaflets 70, 72 may not fully coapt, resulting in mitral regurgitation.

Figure 5:
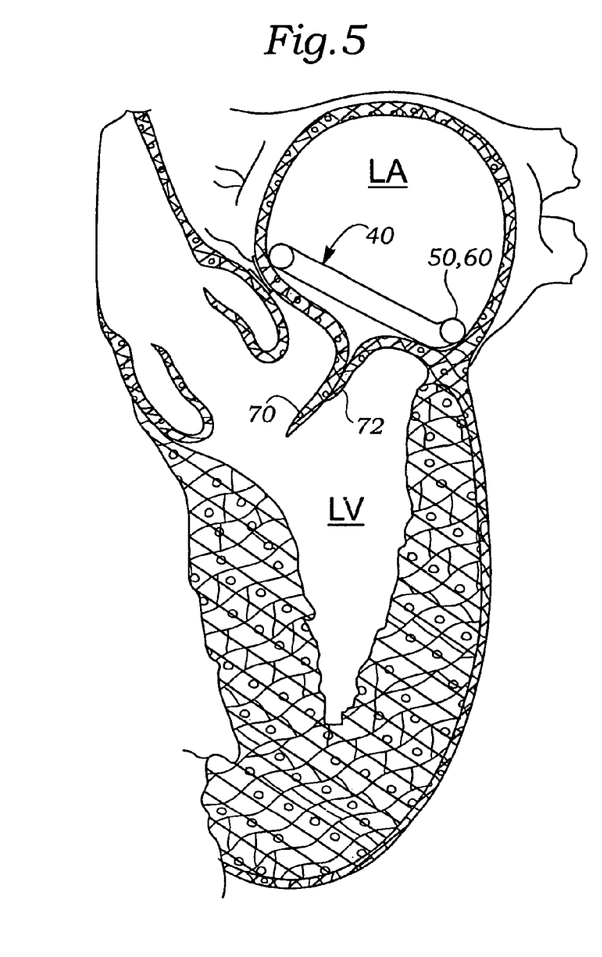
FIG. 5 is an enlarged sectional view similar to FIG. 4 illustrating implantation of a mitral annuloplasty ring of the present invention that helps insure leaflet coaptation.

FIG. 5 illustrates the implantation of the annuloplasty ring 40 in the mitral annulus to correct the condition of FIG. 4. The outward and upward bow 50, 60 of the ring 40 is shown located at the posterior aspect of the annulus. The leaflets 70,72 are shown properly coapting to prevent regurgitation.

The annuloplasty ring 40 is believed to more effectively correct the pathology seen with Barlow's syndrome because it accommodates the longer and/or thicker leaflets instead of attempting to perform a sliding annuloplasty, which is more surgical art than an exact science. The combination of the outward bow and the upward bow on the posterior side of the ring is believed to provide rigid support for the posterior leaflet from which it can more effectively coapt with the anterior leaflet. The annuloplasty ring 40 essentially "pulls" the posterior leaflet outward and upward which reduces its slack or floppiness. Furthermore, the ring 40 should pull the coaptation point outward and upward and away from the LVOT. This should reduce the incidence of SAM and LVOT obstruction and mitral regurgitation post-repair.

It will also be appreciated by those of skill in the relevant art that various modifications or changes may be made to the examples and embodiments described without departing from the intended scope of the invention. In this regard, the particular embodiments of the invention described herein are to be understood as examples of the broader inventive concept disclosed.

What is claimed is:

1. A mitral annuloplasty ring, comprising a ring body made of a material that will substantially resist distortion when subjected to the stress imparted thereon after implantation in the mitral valve annulus of an operating human heart, the ring body defining:
    an anterior segment and a posterior portion opposite the anterior segment;
    right and left sides between the anterior segment and posterior portion;
    a central flow axis having an upward direction and a downward direction, the downward direction corresponding to the direction of blood flow through the mitral valve annulus when the annuloplasty ring is implanted;
    a modified oval shape with a minor axis extending between the anterior segment and posterior portion, and a major axis extending between the sides; and
    a bow in the posterior portion that extends both radially outward and axially upward, wherein an outward convexity of the bow has a smaller radius than adjacent sections, and wherein an axial height h of the bow exceeds about 3 mm.

2. The mitral annuloplasty ring of claim 1, wherein the radially outward portion of the bow is not co-extensive with the axially upward portion.

3. The mitral annuloplasty ring of claim 2, wherein in atrial plan view as seen along the flow axis the ring body has a major axis perpendicular to a minor axis, the major and minor axes being perpendicular to the flow axis, and wherein the ring body has a minor-major dimension ratio of between 3.3:4(82.5%) and 4:4(100%).

4. The mitral annuloplasty ring of claim 1, wherein the axial height h of the bow is between about 3-10 mm.

5. The mitral annuloplasty ring of claim 1, wherein in plan view as seen along the flow axis the ring body has a major axis perpendicular to a minor axis, the major and minor axes being perpendicular to the flow axis, and wherein the ring body has a minor-major dimension ratio of between 3.3:4 (82.5%) and 4:4 (100%).

6. The mitral annuloplasty ring of claim 5, wherein the minor-major dimension ratio is about 3.5:4 (87.5%).

7. The mitral annuloplasty ring of claim 5, wherein the bow is centered about the minor axis and has an angular extent of between 90-110°.

8. The mitral annuloplasty ring of claim 7, wherein the bow has an angular extent of about 100°.

9. The mitral annuloplasty ring of claim 1, wherein in atrial plan view as seen along the flow axis the ring body has an anterior segment generally defined between an anterolateral trigone and a posteromedial trigone, and a posterior portion around the remaining periphery of the ring body and between the trigones, the posterior portion being divided into three sequential segments, $P_1$, $P_2$, and $P_3$, starting from the anterolateral trigone and continuing in a counterclockwise direction, and wherein the bow in the posterior portion is wholly within the middle segment $P_2$ of the posterior portion of the ring.

10. The mitral annuloplasty ring of claim 1, wherein in atrial plan view as seen along the flow axis the ring body has an anterior segment generally defined between an anterolateral trigone and a posteromedial trigone, and a posterior portion around the remaining periphery of the ring body and between the trigones, the posterior portion being divided into three sequential segments, $P_1$, $P_2$, and $P_3$, starting from the anterolateral trigone and continuing in a counterclockwise direction, and wherein the bow in the posterior portion is within the middle segment $P_2$ and at least one other segment $P_1$ or $P_3$ of the posterior portion of the ring.

11. A mitral annuloplasty ring, comprising a ring body made of a material that will substantially resist distortion when subjected to the stress imparted thereon after implantation in the mitral valve annulus of an operating human heart, the ring body defining:
    a rounded ring body having an anterior segment and a posterior portion;
    wherein the ring body is oriented about a central flow axis, the flow axis defining an upward direction and a downward direction, the downward direction corresponding to the direction of blood flow through the mitral valve annulus, wherein in atrial plan view as seen along the flow axis the anterior segment is generally defined between an anterolateral trigone and a posteromedial trigone, and the posterior portion extends around the remaining periphery of the ring body and between the trigones, the posterior portion being divided into three sequential segments, $P_1$, $P_2$, and $P_3$, starting from the anterolateral trigone and continuing in a counterclockwise direction; and,
    wherein in the posterior portion the ring body bows upward out of a plane perpendicular to the central flow axis and wholly within the middle segment $P_2$ of the posterior portion of the ring, and also has a radially outward curve more pronounced than adjacent sections.

12. The mitral annuloplasty ring of claim 11, wherein an axial height h of the upward bow exceeds about 3 mm.

13. The mitral annuloplasty ring of claim 12, wherein the axial height h of the upward bow is between about 3-10 mm.

14. The mitral annuloplasty ring of claim 12, wherein in atrial plan view as seen along the flow axis the ring body has a major axis perpendicular to a minor axis, the major and minor axes being perpendicular to the flow axis, and wherein the ring body has a minor-major dimension ratio of between 3.3:4 (82.5%) and 4:4 (100%).

15. The mitral annuloplasty ring of claim 14, wherein the minor-major dimension ratio is about 3.5:4 (87.5%).

16. The mitral annuloplasty ring of claim 14, wherein the bow is centered about the minor axis and has an angular extent of between 90-110°.

17. The mitral annuloplasty ring of claim 11, wherein the radially outward curve is not co-extensive with the upward bow.

18. A mitral annuloplasty ring, comprising a ring body made of a material that will substantially resist distortion when subjected to the stress imparted thereon after implantation in the mitral valve annulus of an operating human heart, the ring body defining:
a modified oval-shaped ring body oriented about a central flow axis, the flow axis defining an upward direction and a downward direction, the downward direction corresponding to the direction of blood flow through the mitral valve annulus from the left atrium to the left ventricle, and wherein in plan view as seen along the flow axis the ring body has a major axis perpendicular to a minor axis, the major and minor axes being perpendicular to the flow axis,
the ring body having in atrial plan view an anterior segment generally defined between an anterolateral trigone and a posteromedial trigone, and a posterior portion around the remaining periphery of the ring body and between the trigones, the posterior portion being divided into three sequential segments, $P_1$, $P_2$, and $P_3$ starting from the anterolateral trigone and continuing in a counterclockwise direction, the segments generally corresponding to the size of the native posterior leaflet cusps, wherein the minor axis intersects both the anterior segment and the $P_2$ segment of the posterior portion; and,
wherein the ring body lies substantially in a plane defined by the major and minor axes or in a saddle-shaped three-dimensional surface except for the $P_2$ segment of the posterior portion located which is deflected upward and outward in a more pronounced, smaller radius curve with respect to the adjacent sections of the ring body, wherein an axial height h of the upward deflection exceeds about 3 mm.

19. The mitral annuloplasty ring of claim 18, the outward deflection is not co-extensive with the upward deflection.

20. The mitral annuloplasty ring of claim 18, wherein the axial height h of the upward deflection is between about 3-10 mm.

21. The mitral annuloplasty ring of claim 18, wherein in atrial plan view as seen along the flow axis the ring body has a major axis perpendicular to a minor axis, the major and minor axes being perpendicular to the flow axis, and wherein the ring body has a minor-major dimension ratio of between 3.3:4 (82.5%) and 4:4 (100%).

22. The mitral annuloplasty ring of claim 21, wherein the minor-major dimension ratio is about 3.5:4 (87.5%).

23. The mitral annuloplasty ring of claim 21, wherein the outward deflection is centered about the minor axis and has an angular extent of between 90-110°.

24. A mitral annuloplasty ring, comprising a ring body made of a material that will substantially resist distortion when subjected to the stress imparted thereon after implantation in the mitral valve annulus of an operating human heart, the ring body defining:
an anterior segment and a posterior portion opposite the anterior segment;
right and left sides between the anterior segment and posterior portion;
a central flow axis having an upward direction and a downward direction, the downward direction corresponding to the direction of blood flow through the mitral valve annulus when the annuloplasty ring is implanted;
a modified oval shape with a minor axis extending between the anterior segment and posterior portion, and a major axis extending between the sides, wherein in plan view as seen along the flow axis the ring body has a major axis perpendicular to a minor axis, the major and minor axes being perpendicular to the flow axis, and wherein the ring body has a minor-major dimension ratio of between 3.3:4 (82.5%) and 4:4 (100%); and
a bow in the posterior portion that extends both radially outward and axially upward, wherein an outward convexity of the bow has a smaller radius than adjacent sections.

25. The mitral annuloplasty ring of claim 24, wherein the minor-major dimension ratio is about 3.5:4 (87.5%).

26. The mitral annuloplasty ring of claim 24, wherein the bow is centered about the minor axis and has an angular extent of between 90-110°.

27. The mitral annuloplasty ring of claim 24, wherein the radially outward portion of the bow is co-extensive with the axially upward portion.

28. The mitral annuloplasty ring of claim 24, wherein the radially outward portion of the bow is not co-extensive with the axially upward portion.

29. The mitral annuloplasty ring of claim 24, wherein the axial height h of the bow is between about 3-10 mm.

30. The mitral annuloplasty ring of claim 24, wherein in atrial plan view as seen along the flow axis the anterior segment is generally defined between an anterolateral trigone and a posteromedial trigone, and the posterior portion extends around the remaining periphery of the ring body and between the trigones, the posterior portion being divided into three sequential segments, $P_1$, $P_2$, and $P_3$, starting from the anterolateral trigone and continuing in a counterclockwise direction, and wherein the bow in the posterior portion is wholly within the middle segment $P_2$ of the posterior portion of the ring.

31. The mitral annuloplasty ring of claim 24, wherein in atrial plan view as seen along the flow axis the anterior segment is generally defined between an anterolateral trigone and a posteromedial trigone, and the posterior portion extends around the remaining periphery of the ring body and between the trigones, the posterior portion being divided into three sequential segments, $P_1$, $P_2$, and $P_3$, starting from the anterolateral trigone and continuing in a counterclockwise direction, and wherein the bow in the posterior portion is within the middle segment $P_2$ and at least one other segment $P_1$ or $P_3$ of the posterior portion of the ring.

32. The mitral annuloplasty ring of claim 31, wherein the bow in the posterior portion extends into both the first and third segments $P_1$ and $P_3$ of the posterior portion.

33. The mitral annuloplasty ring of claim 31, wherein the bow in the posterior portion extends into only one of the first and third segments $P_1$ and $P_3$ of the posterior portion.

34. The mitral annuloplasty ring of claim 31, wherein the radially outward portion of the bow extends into only one of the first and third segments $P_1$ and $P_3$ of the posterior portion.

35. A mitral annuloplasty ring, comprising a ring body made of a material that will substantially resist distortion when subjected to the stress imparted thereon after implantation in the mitral valve annulus of an operating human heart, the ring body defining:
a rounded ring body having an anterior segment and a posterior portion;
wherein the ring body is oriented about a central flow axis, the flow axis defining an upward direction and a downward direction, the downward direction corresponding to the direction of blood flow through the mitral valve annulus; and, wherein in the posterior portion the ring body bows upward out of a plane perpendicular to the central flow axis to an axial height h of that exceeds about 3 mm and also has a radially outward curve more pronounced than adjacent sections.

36. The mitral annuloplasty ring of claim 35, wherein the axial height h of the upward bow is between about 3-10 mm.

37. The mitral annuloplasty ring of claim 35, wherein in atrial plan view as seen along the flow axis the ring body has a major axis perpendicular to a minor axis, the major and minor axes being perpendicular to the flow axis, and wherein the ring body has a minor-major dimension ratio of between 3.3:4 (82.5%) and 4:4 (100%).

38. The mitral annuloplasty ring of claim 35, wherein the minor-major dimension ratio is about 3.5:4 (87.5%).

39. The mitral annuloplasty ring of claim 35, wherein the bow is centered about the minor axis and has an angular extent of between 90-110°.

40. The mitral annuloplasty ring of claim 35, wherein the radially outward curve is not co-extensive with the upward bow.

* * * * *